United States Patent [19]

van Dalen et al.

[11] 4,028,928

[45] June 14, 1977

[54] METHOD OF DETECTING VERY SMALL GAS LEAKAGES THROUGH A LIQUID SEAL AROUND A PASSAGE

[75] Inventors: Adrianus van Dalen, Schoorl; Johannes W. H. van der Bergh, Bergen N. H., both of Netherlands

[73] Assignee: Neratoom B.V., The Hague, Netherlands

[22] Filed: Mar. 3, 1975

[21] Appl. No.: 554,695

[30] Foreign Application Priority Data

Mar. 11, 1974   Netherlands .................... 7403213

[52] U.S. Cl. ............................................. 73/40.7
[51] Int. Cl.² ....................................... G01M 3/20
[58] Field of Search ............ 73/40.7; 250/302, 393

[56] References Cited

UNITED STATES PATENTS 3,585,845   6/1971   Cornell ............................ 73/40.7
3,597,611   8/1971   Harman ........................... 250/303

Primary Examiner—S. Clement Swisher
Attorney, Agent, or Firm—Cushman, Darby and Cushman

[57] ABSTRACT

The invention relates to the detection of very small gas leakages through liquid seals around a passage, which seal may be situated around a shaft.

Before it was not easy to detect gas leakages to the environment through liquid seals from radio actively contaminated spaces.

Said disadvantage can be avoided, by determining the gas leakage to the environment through a liquid seal by applying at one side of the seal a gas activable by neutrons and subsequently determining the concentration of the said gas in the sealing liquid as function of the time.

7 Claims, 1 Drawing Figure

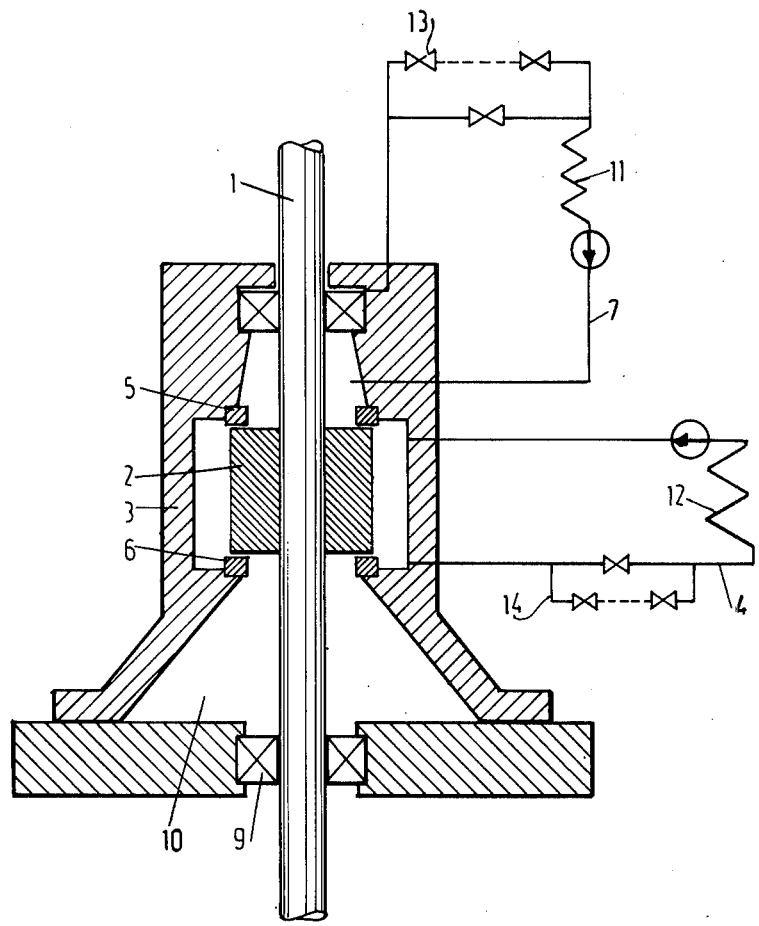

METHOD OF DETECTING VERY SMALL GAS LEAKAGES THROUGH A LIQUID SEAL AROUND A PASSAGE

The invention relates to the detection of very small gas leakages through a liquid seal around a passage. Very small gas leakages are defined as gas leakages ranging from 0.1 to 10 cubic centimeters (as related to normal temperature and pressure). The limit of detection of the gas leakage depends on the amount of sealing liquid used. It used to be virtually impossible to determine these small gas leakages through liquid seals around passages.

In view of the growing number of nuclear plants in which liquid seals are used, it is of major importance to make exact measurements of the maximum radioactivity transmitted as a result of gas diffusion.

The sensitivity of the known helium leakage testing method has been found inadequate in demonstrating a leak in a liquid seal for nuclear applications, so that nothing was recorded.

Other possible applications of the new leakage testing method may be found in chemical and nuclear processing techniques which are implemented with the use of poisonous, aggressive or radioactive gases.

The invention aims at solving the above-mentioned problem by providing a novel method of determining very small gas leakages.

According to the invention, a gas or gas mixture which can be activated by neutrons is applied to one side of the liquid seal, whereupon the concentration of this gas (mixture) in the sealing liquid is determined as a function of time.

The novel method has the advantage that there is no need to provide a gastight auxiliary closure for measuring an increase of the leaking gas in this auxiliary space. Providing a gastight auxiliary closure is especially a problem with shaft passages. The reason is that the shaft must then also be sealed with respect to the environment on the upper side of the gastight space. Although the principal application of the novel leak-tightness measurement relates to shaft passages, applications definitely are also conceivable for liquid-sealed flange passages, for sealing a piston passage and possibly for other liquid seals as well.

Gases capable of being used and of being activated by neutrons include argon, krypton and xenon, and gases containing fluorine, chlorine, bromine or iodine. Regarding argon gas it is to be noted that this gas or element comprises three stable isotopes: $^{36}Ar$, $^{38}Ar$, $^{40}Ar$. The last isotope is important for the analysis by activation with thermal neutrons. It occurs for 29.6 percent in the natural mixture of isotopes and has an active cross section for the capture of thermal neutrons of $(0.53 \pm 0.02) \cdot 10^-$ sq. cm.

Neutron capture leads to the formation of the isotope $^{41}Ar$, which as a result of $\beta$ decay passes into the stable isotope $^{41}K$. The gamma radiation of 1.283 NeV which accompanies this disintegration is used for measuring the degree of activity of argon. The half-live of 1.837 hours is very favourable: only a short time of irradiation is necessary, and the measurement can be repeated after one day without any correction for the activity of the remaining radiation. Since short times of irradiation are sufficient, there appears no disintegration in the material in which argon must be determined: this means for this series of measurements that there is no need to separate argon from the oil samples. In an experimental irradiation of an oil sample it was also found that neutron irradiation does not create any activity which has a disturbing effect on the activity measurement of argon.

Suitable halogen-containing gases of which the concentration can be satisfactorily determined by neutron activation in a sealing oil consisting of hydrocarbons are gaseous halogenated hydrocarbons. Freon gas is particularly indicated in this respect.

The absolute gas leakage to the environment can be calculated from the course of concentration of the gas dissolved in the sealing liquid as a function of time based on diffusion of the gas (mixture) from the gas space for the sealing liquid to the environment.

For a relatively simple case, the gas concentration as a function of time is determined by the equation $$dx/dt = k_1 (C - x) - k_2 x, \qquad (1)$$

where:
$x$ is the gas concentration in the sealing liquid at the time t;
$t$ is the time;
$C$ is the final gas concentration in the sealing liquid if no gas leaks out;
$k_1$ is the "gas leak-in constant" for gas leaking from the gas space into the sealing liquid;
$k_2$ is the "gas leak-out constant" for gas leaking from the sealing liquid to the environment.

Solution of Equation (1) yields:

$$x = \frac{k_1 C}{k_1 + k_2} (1 - e^{-(k_1 + k_2)t}) + C_1. \qquad (2)$$

The integration constant $C_1$ relates to the amount of gas to be measured which is already present in the sealing liquid. With the use of argon as detector gas, this is the amount which is naturally present because the sealing liquid has been in contact with air prior to its use. By setting $t = 0$ in Equation (2), the integration constant $C_1$ is found to have the value of $x$ at the time zero: $x_0$.

If $t$ is very high ($t = \infty$), Equation (2) passes over into $$x - x_0 = \frac{k_1 C}{k_1 + k_2}. \qquad (3)$$

Leakage to the environment at the time $t = \infty$ is now described by $$k_2 (x_\infty - x_0) = k_2 \frac{k_1 C}{k_1 + k_2}. \qquad (4)$$

The following method of calculation is now applied to Equation (2) with $C_1 = x_0$: the measured values $x - x_0$ are divided by the function $1 - e^{-yt}$, $y$ being varied. For the required value of $y$, the quotient mentioned must yield a constant, which can be verified by, for example, the method of least squares. The value of $y$ which satisfies this requirement as well as possible is then at the same time the value of $k_1 + k_2$. The appertaining quotient has the value $(k_1 C/k_1 + k_2)$.

This process can be carried out graphically as well as numerically. The factor $(k_1 C/k_1 + k_2)$ at the same time is the value of $x_\infty$ or $(k_1 C/y) = x$, where $k_1 + k_2 = y$.

Since a stationary state of leakage prevails at the time $t = \infty$ leakage into the liquid seal must have the same value as the leakage towards the environment: $k_1(C - x_\infty) = k_2 x_\infty$ which, converted, is equivalent to $$k_1 C - k_1 x_\infty = y x_\infty - (y - k_2) x_\infty = k_2 x_\infty$$

From this equation, $k_2$ can be solved, whereupon the leakage value is obtained by substitution of $k_2$ into Equation (4):

$$k_2 x = k_2 (k_1 C/k_1 + k_2).$$

It should be borne in mind that the value of C cannot be determined independently. This concentration value is determined by the condition in which the gas leaks into and out of the sealing liquid. This type of processes takes place in liquid films, in which the conditions of temperature and pressure differ from those in the principal mass of the sealing liquid. A liquid seal for an aggressive gas can be provided with elements for sampling.

The expression sealing liquid in confined space which has been discussed throughout also includes and allows for any possible gas spaces in such a system, which likewise constitute factors in the determinations of concentration.

The invention is explained in the following description of the FIGURE.

In the FIGURE, the number 1 indicates a shaft which is provided with a ring 2 that is rigidly attached to it. Two sealing rings 5 and 6, rigidly connected to a housing 3, are provided opposite the ring 2. Sealing oil in two oil circuits 7 and 4, shown schematically, is injected between the ring seals 2 and 5 and 2 and 6. The oil serves both for lubrication and cooling. The shaft 1 is supported by means of bearings 8 and 9.

Underneath the lower seal 6 is a gas space 10, which also extends below the bearing 9. During the determination of leak tightness the gas space 10 contains argon gas.

The oil circuits 7 and 4 are equipped with heat exchangers 11 and 12 for cooling the oil and with sample extraction systems 13 and 14 for oil sampling. The oil samples extracted from the oil circuits 7 and 4 at different times in the course of the measurement are used for determining the argon concentration by activation.

We claim:

1. Method of detecting very small gas leakages through a liquid seal around an element, at which element at the same time a gas space is present, comprising applying a gas or gas mixture capable of being activated by neutrons to one side of the said liquid seal in the gas space, and thereafter determining the concentration of this gas or gas mixture in the sealing liquid as a function of time by means of neutron activation.

2. Method according to claim 1, wherein the liquid seal is provided around a shaft.

3. Method according to claim 1, wherein the gas or gas mixture which is capable of being activated comprises argon, krypton or xenon or a gas containing fluorine, chlorine, bromine or iodine.

4. Method according to claim 1, wherein the gas or gas mixture which is capable of being activated comprises one or more gaseous halogenated hydrocarbons.

5. Method according to claim 1, wherein the gas leakage is calculated from the curve showing the concentration of the dissolved gas as a function of time based on diffusion of the gas (mixture) from the gas space in the sealing liquid to the environment in case no auxiliary closure is used.

6. Method according to claim 1, wherein the gas leakage to the environment is determined by solving the equation $$dx/dt = k_1 (C - x) - k_2 x$$

or a similar equation, in which equation $x$ represents the gas concentration in the sealing liquid, $t$ the time, $C$ a final gas concentration in the sealing liquid if no gas leaks out, and $k_1$ and $k_2$ represents "leakage constants" for leakage from the gas space into the sealing liquid and for leakage from the sealing liquid to the environment.

7. In combination with an annular liquid seal and, a gas space with means for admitting neutron activable gas in the gas space and means for extracting samples from the sealing liquid for neutron activation.

* * * * *